(12) United States Patent
Andersen et al.

(10) Patent No.: US 11,161,139 B2
(45) Date of Patent: Nov. 2, 2021

(54) METHOD AND SYSTEM FOR TREATING A SURFACE

(71) Applicant: INNANO AS, Oslo (NO)

(72) Inventors: Aage Bjorn Andersen, Oslo (NO); Kingsley Iwu, Oslo (NO)

(73) Assignee: MOSSHYDRO AS

( * ) Notice: Subject to any disclaimer, the term of this patent is extended or adjusted under 35 U.S.C. 154(b) by 0 days.

(21) Appl. No.: 16/327,474

(22) PCT Filed: Aug. 17, 2017

(86) PCT No.: PCT/EP2017/070871
§ 371 (c)(1),
(2) Date: May 6, 2019

(87) PCT Pub. No.: WO2018/036907
PCT Pub. Date: Mar. 1, 2018

(65) Prior Publication Data
US 2019/0176182 A1  Jun. 13, 2019

(30) Foreign Application Priority Data
Aug. 22, 2016  (GB) ..................................... 1614332

(51) Int. Cl.
*B05C 3/109* (2006.01)
*B05C 3/09* (2006.01)
(Continued)

(52) U.S. Cl.
CPC ................ *B05C 3/109* (2013.01); *B05C 3/09* (2013.01); *B05C 7/04* (2013.01); *B05D 1/18* (2013.01);
(Continued)

(58) Field of Classification Search
CPC . B05D 1/18; B05D 1/62; B05D 3/061; B05D 3/065; B05D 7/22; B05D 7/227;
(Continued)

(56) References Cited

U.S. PATENT DOCUMENTS 2,206,778 A  7/1940  Kronquest
2,862,236 A  12/1958  Shapero
(Continued)

FOREIGN PATENT DOCUMENTS

CA  1100369       5/1981
CA  1100369 A  *  5/1981  ............. B05C 3/109
(Continued)

OTHER PUBLICATIONS

PCT International Search Report and Written Opinion, PCT International Application No. PCT/EP2017/070871, dated Nov. 15, 2017, 14 pages.

(Continued)

*Primary Examiner* — William P Fletcher, III
(74) *Attorney, Agent, or Firm* — McDonnell Boehnen Hulbert & Berghoff LLP (57) ABSTRACT

A method of applying a treatment to a surface of an open body having a volume within an interior of the open body comprises; providing an inner structure (110) shaped to complement the shape of the interior of the open body and to fill a major portion of the volume or a major portion of a width of the interior of the open body; positioning the inner structure (110) within the open body in order to form a treatment fluid inner volume comprising an inner space (150) confronting an inner surface within the interior of the open body; and introducing a treatment fluid into the treatment fluid inner volume to thereby modify the inner surface of the open body by applying the treatment using the treatment fluid. Optionally, the method includes providing a (Continued)

tank (120) shaped to complement and contain the open body; positioning the open body within the tank (120) in order to form a treatment fluid outer volume comprising an outer space confronting the outer surface of the open body; and introducing the treatment fluid into the treatment fluid outer volume to thereby modify the outer surface of the open body by applying the treatment using the treatment fluid.

14 Claims, 3 Drawing Sheets

(51) Int. Cl.
| | |
|---|---|
| B05D 7/22 | (2006.01) |
| B05D 1/18 | (2006.01) |
| B05C 7/04 | (2006.01) |
| C23C 16/04 | (2006.01) |
| B08B 9/08 | (2006.01) |
| C23C 16/455 | (2006.01) |
| C23C 16/505 | (2006.01) |
| B08B 9/00 | (2006.01) |
| B08B 3/12 | (2006.01) |
| B08B 1/00 | (2006.01) |
| B08B 9/087 | (2006.01) |

(52) U.S. Cl.
CPC ................. *B05D 7/22* (2013.01); *B08B 3/12* (2013.01); *B08B 9/00* (2013.01); *B08B 9/08* (2013.01); *C23C 16/045* (2013.01); *C23C 16/455* (2013.01); *C23C 16/45517* (2013.01); *C23C 16/505* (2013.01); *B08B 1/002* (2013.01); *B08B 9/087* (2013.01); *B08B 2209/005* (2013.01); *B08B 2209/08* (2013.01)

(58) Field of Classification Search
CPC ............ B05D 2254/02; B05D 2254/06; B05D 2259/00; B05C 3/02; B05C 3/04; B05C 3/05; B05C 3/09; B05C 3/109; B05C 7/04; B05C 13/025; B05B 13/06; B05B 13/069; C23C 16/045; C23C 16/455; C23C 16/45517

See application file for complete search history.

(56) References Cited

U.S. PATENT DOCUMENTS

| | | | | |
|---|---|---|---|---|
| 4,026,311 A | * | 5/1977 | Jackson | B08B 9/08 134/48 |
| 4,042,416 A | * | 8/1977 | Miskech | B08B 3/02 134/10 |
| 4,130,084 A | | 12/1978 | Hoelen | |
| 4,152,173 A | * | 5/1979 | Jackson | B05D 1/18 118/59 |
| 4,338,879 A | | 7/1982 | Makeev et al. | |
| 4,746,538 A | * | 5/1988 | Mackowski | C03C 17/22 427/577 |
| 4,965,099 A | * | 10/1990 | Bornhorst | B05C 3/02 118/408 |
| 5,094,891 A | | 3/1992 | Wren | |
| 5,681,391 A | * | 10/1997 | Mistrater | B05C 3/109 118/400 |
| 5,693,372 A | * | 12/1997 | Mistrater | B05C 3/109 118/429 |
| 5,753,312 A | | 5/1998 | Chambers et al. | |
| 5,849,366 A | * | 12/1998 | Plester | C23C 16/045 427/491 |
| 6,149,982 A | * | 11/2000 | Plester | B05D 1/62 427/171 |
| 6,214,419 B1 | * | 4/2001 | Dinh | B05C 3/09 427/430.1 |
| 6,270,850 B1 | | 8/2001 | Cai et al. | |
| 6,294,226 B1 | * | 9/2001 | Shimamura | B29C 59/142 118/723 E |
| 6,302,306 B1 | | 10/2001 | Lin et al. | |
| 6,312,522 B1 | * | 11/2001 | Dinh | B05C 3/09 118/407 |
| 6,827,972 B2 | * | 12/2004 | Darras | B05D 1/62 427/237 |
| 2002/0176947 A1 | * | 11/2002 | Darras | C23C 16/26 427/569 |
| 2004/0146666 A1 | * | 7/2004 | Hama | C23C 16/26 428/34.1 |
| 2004/0149225 A1 | * | 8/2004 | Weikart | C09D 4/00 118/723 MW |
| 2004/0247948 A1 | * | 12/2004 | Behle | C23C 16/401 428/701 |
| 2005/0118365 A1 | * | 6/2005 | Miyazaki | C23C 16/26 428/34.1 |
| 2005/0229851 A1 | * | 10/2005 | Hama | C23C 16/26 118/723 E |
| 2006/0108034 A1 | * | 5/2006 | Frommann | C23C 2/02 148/565 |
| 2007/0240783 A1 | * | 10/2007 | Mouchelet | C23C 16/511 141/82 |
| 2009/0280276 A1 | * | 11/2009 | Noll | C23C 16/509 428/34.1 |
| 2010/0298738 A1 | * | 11/2010 | Felts | B65D 25/14 600/576 |
| 2011/0209746 A1 | | 9/2011 | Zhang et al. | |

FOREIGN PATENT DOCUMENTS

| | | |
|---|---|---|
| CA | 1100369 A | 5/1981 |
| CN | 1775376 A | 5/2006 |
| CN | 1822905 A | 8/2006 |
| DE | 102012206059 A1 | 10/2013 |
| JP | S60158452 A | 8/1985 |
| JP | S62-284081 | 12/1987 |
| JP | H2-175876 | 7/1990 |
| JP | 2008-223092 | 9/2008 |
| JP | 2013-528117 | 7/2013 |
| JP | 2014-34685 | 2/2014 |
| WO | WO 2011/143329 | 11/2011 |

OTHER PUBLICATIONS

GB Search Report, GB Application No. 1614332.3, dated Jan. 12, 2017, 4 pages.
Japanese Office Action dated Jun. 8, 2021 for Japanese Application No. 2019-532174, 15 pages.
Second Office Action dated Jun. 21, 2021, in corresponding application Chinese Patent Application No. CN201780065050.X, 29 pages.
Jingfang et al., "Optical Anti-counterfeiting Technology and its Application", National Defense Industry Press, 2011, 127-131.

* cited by examiner

METHOD AND SYSTEM FOR TREATING A SURFACE

The inventions relates to a method and system for applying a treatment to a surface. Particularly it applies to applying a treatment fluid to a surface of an open body.

The treatment of a surface of an article is often necessary for those articles to be used in the intended manner for their intended purpose. For example, cleaning, coating, or functionalizing surfaces may be necessary. For such treatment, a treatment fluid is often applied to the surface to be treated. A typical method of applying a treatment fluid to a surface comprises saturating the surface with the fluid by dipping the article to be treated into a reservoir of the treatment fluid or introducing and filling the volume of space confronting the surface of the article with the treatment fluid. The latter can be accomplished by pumping or pouring the fluid into the volume of space. For simplicity, we broadly use dipping here to include any such process used to saturate the surface of an article with a treatment fluid. Dipping can be faster and easier than other methods such as spraying the treatment fluid onto the surface. It can also more reliably provide an even coverage over a large surface even if the surface is uneven or perforated.

However, articles which need to be treated can vary in shape and size, and hence dipping such articles requires a reservoir of fluid sufficiently large to accommodate all such articles. This in turn requires a large volume of treatment fluid to be available.

Many articles which need to be treated are formed as open bodies, such as cylinders open at one or both ends, or tubes, or hemispheres etc. The hollow nature of these open bodies further necessitates the supply of a large volume of treatment fluid for dipping, since the treatment fluid will enter inside the open body of the article.

Treatment fluids may be expensive, or have a limited lifetime, and so supplying them in large quantities can be inefficient. Often, as little as 1% or less of the fluid supplied may be consumed in actually treating the surface of the article. In addition, it can be difficult to achieve an even/uniform treatment of the surface for certain shapes of articles.

According to a first aspect of the present invention there is provided a method of applying a treatment to a surface of an open body having a volume within an interior of the open body, the method comprising; providing an inner structure shaped to complement the shape of the interior of the open body and to fill a major portion of the volume or a major portion of a width of the interior of the open body; positioning the inner structure within the open body in order to form a treatment fluid inner volume comprising an inner space confronting an inner surface within the interior of the open body; and introducing a treatment fluid into the treatment fluid inner volume to thereby modify the inner surface of the open body by applying the treatment using the treatment fluid.

With this method the amount of treatment fluid required to treat the surface can be greatly reduced and/or the uniformity of the treatment can be increased. This has various advantages. A uniform treatment is beneficial for efficient use of materials and for improving the quality of the final product. The treatment fluid can be expensive and/or energy intensive to produce or discard/recycle. The treatment fluid application process can naturally produce a lot of waste—either due to the treatment fluid having a very short life time/not being reusable or generation of waste by-products. Using a smaller volume hence has benefits for costs and energy usage, as well as environmental benefits where the treatment fluid can have an adverse environmental impact. The requirements relating to storage of the fluid before and after use are also reduced.

With the proposed method it is no longer necessary to fully surround and fill the entire volume of the open body. Instead a major part of the volume or a major part of the width of the open body is taken up by the inner structure. Thus, it may be that only the volume immediately adjacent to the inner surface is filled with the fluid. The inner surface may be the entire interior surface or it may be only a part of the interior surface. In the latter case the inner structure may be arranged to contact other parts of the interior surface in order to prevent the treatment fluid from touching those other parts.

The method may also provide for a more even treatment of the surface of the open body. This is because the surface of the open body can be closer to and/or more evenly spaced from the inner structure. In circumstances where the inner structure performs an active role in the treatment, for example where a plasma treatment is used and/or where electrical or ultrasonic energy is input via the inner structure, then it is an advantage to reduce the distance between the inner structure and the surface to be treated as well as to make this distance more even.

The open body may comprise a continuous surface, or may be formed of a mesh, or a textured surface or the like. Positioning of the inner structure to fill a major portion of the volume of the open body may comprise moving the open body about the inner structure while the inner structure remains stationary, or may comprise moving the inner structure while the open body remains stationary, or may comprise moving both the open body and the inner structure. The open body may be hollow. The major portion of the width of the open body filled by the inner structure should be more than 50% of the width and may be about 60% or 80% of the width of the open body, optionally about 90% of the width of the open body. Thus, the inner space to be filled by the treatment fluid may have a width that is about 20%, 10% or 5% of the width of the open body, i.e. a total extent summed on both sides of the inner structure that is about 40%, 20% or 10% of the width of the open body. The width may for example be a diameter in the case of a circular geometry. It will be noted that an inner structure occupying a major portion of the width of the open body need not necessarily occupy a major portion of the volume. For example, with a circular geometry then an inner structure of 60% of the diameter of the open body would occupy 36% of the volume. In the case where the inner structure occupies a major portion of the volume of the open body filled by the inner structure then the major portion may be about 60% or 80% of the volume of the open body, optionally about 90% of the volume of the open body, optionally about 95% of the volume of the open body. Thus, the inner space may have a total volume that is about 20%, 10% or 5% of the volume of the open body.

The inner space may be a relatively narrow space, i.e. an inner narrow space with a lesser width than the width of the open body and optionally a width that results in the volume of the inner narrow space occupying a minor portion of the volume of the open body.

The inner structure may be inflatable, and the step of positioning the inner structure may comprise inflating the inner structure. The inflatable inner structure may be shaped to complement the shape of the interior of the open body and/or the required inner surface for treatment in its inflated state. In this way, the inner structure may be inserted into the open body and inflated within the open body. Therefore, the opening in the open body may be smaller than the size of the inflated inner structure. The opening in the open body may be any hole into the hollow interior of the body. Therefore, the disclosed method may be employed on a wide variety of open bodies, including those for which the opening is large enough to provide unobstructed access to substantially the whole interior of the body, as well as those for which the opening is only a small hole into the interior of a hollow body.

Alternatively, the inner structure may be rigid. It may therefore require a particular orientation with respect to the open body to be inserted therein, and the inner structure and opening may cooperate to help guide the open body during positioning. The opening of the open body may be shaped so as to permit insertion of the inner structure so as to fill the major portion of the volume of the open body.

The method may further comprise; providing a tank shaped to complement and contain the open body; positioning the open body within the tank in order to form a treatment fluid outer volume comprising an outer space confronting an outer surface of the open body; and introducing the treatment fluid into the treatment fluid outer volume to thereby modify the outer surface of the open body by applying the treatment using the treatment fluid. The outer space may have a similar width to the inner space. It may be a relatively narrow space, i.e. an outer narrow space with a lesser width than the width of the open body and optionally a width that results in the volume of the outer narrow space occupying a minor portion of the volume of the tank.

The use of a tank may allow for a more efficient and/or more effective treatment of the outer surface of the open body as well as the inner surface of the open body, especially when the inner walls of the outer tank, the outer walls of the inner structure and the walls of the open body act as electrodes for electrochemical or electromagnetic treatments. In this case, the uniformity of the distance between the open body and the tank and the distance between the open body and the inner structure at any point ensures uniform treatment.

In a modification of the treatment of the outer surface the treatment fluid used to treat the outer surface may be different to the treatment fluid used to treat the inner surface. In this case there should be no fluid communication within the inner volume and the outer volume.

The open body may therefore be nested between the tank and the inner structure during treatment, with the narrow outer space defined between an inner surface of the tank and the outer surface of the open body, and the inner space defined between the inner surface of the open body and an outer surface of the inner structure. The narrow inner space and/or the outer space, where present, may extend across the inner surface with an even width for the inner space, such that the distance between the inner structure and/or the tank and open body at each point is approximately the same. This can help ensure an even treatment effect, for example in cases where some chemical reaction occurs between the material of the open body and the treatment fluid. The inner space and the outer space may be in fluid communication, for example if the open body comprises a mesh or a membrane with pores etc. The inner space and outer space may be in fluid communication by the opening of the open body.

The positioning of the inner structure within the open body and the positioning of the open body within the tank may be carried out simultaneously, for example in the case that the inner structure is fixed relative to the tank and the open body is inserted into a space defined between the tank and the inner structure. The space between the tank and the inner structure may therefore be divided by the open body into the inner space and the outer space. The steps of introducing the treatment fluid to into the treatment fluid inner volume and introducing the treatment fluid to into the treatment fluid outer volume may also be carried out at the same time.

Applying the treatment may comprise coating, cleaning, and/or functionalizing the surface of the open body. The treatment fluid may be a liquid, gas or plasma. In this context references to fluid should be taken to include plasma. In an example, to functionalise the surface of the open body the treatment fluid may comprise hydroxyl groups in order to make the surface hydrophilic. In another example, plasma enhanced chemical vapour deposition (PECVD) is used and the treatment fluid may hence be a plasma with the open body and/or the inner structure being used as an electrode as discussed further below.

The method may also comprise applying ultrasonic waves to the treatment fluid and/or open body. The application of ultrasonic waves can aid in forcing the treatment fluid (liquid) against the open body, in order to functionalise the surface, and/or aid the deposition of substances to coat the surface of the open body. For example, if the open body comprises a mesh with holes, or a surface with pores and/or crevices, then ultrasonic waves aid in distributing the treatment fluid into and around the entire surface of the open body without blocking or clogging the holes/pores/crevices. Some treatment fluids, specifically liquid solutions, may contain dispersed particles as suspensions. Ultrasonic waves can also be used to prevent the particles from settling (dropping) out of the solution. Ultrasonication is particularly important during cleaning of an article with tiny pores and crevices.

The method may comprise applying heat to the treatment fluid and/or open body, which may also aid in distributing the treatment fluid evenly over the entire surface of the open body. The method may also comprise heating the treatment fluid and/or open body after the treatment fluid is applied to the open body in order to cure or anneal a coating on the open body. Heating may also be used to dry a treated article, including drying after cleaning as well as drying after coating or other treatment The method may comprise applying ultraviolet (UV) radiation to the treatment fluid applied to the surface of the open body, for example in order to cure the coating on the open body and/or to polymerise an applied coating. UV radiation may also be used to clean, functionalise or aid the deposition of substances to coat the surface of the open body, in conjunction or complementary to a treatment fluid.

A step of centrifugation may be used in order to promote interaction of the treatment fluid with the surface of the open body. For example this may have benefits when the treatment fluid is a mixture and it is desired to promote contact of denser elements of the mixture with the surface. It may also have benefits when the treatment fluid is a plasma and the treatment includes interaction of the plasma with the surface of the open body.

The method may include compression of the treatment fluid, for example by application of pressure to the fluid via an inlet to the volume, by expansion of the inner structure and/or by contraction of the tank (when present). This can have similar effects to centrifugation, for example when using a liquid as the treatment fluid, but has the added advantage of not forming foams.

The method may include applying a vacuum as a part of a sequence of treatment steps. For example, a vacuum may be used: to remove air or any other gas present before the treatment fluid is introduced, which may enhance contact of the fluid with the surface of the open body especially when the surface is uneven; to draw treatment fluid into the treatment volume(s); and/or for removing excess fluid from the coated article and/or treatment space after treatment.

In some examples the method may include applying a plasma, for example in context of plasma enhanced chemical vapour deposition (PECVD). The plasma may be generated in a plasma generator before being passed to the treatment fluid volume. Alternatively the plasma may be generated within the treatment fluid volume via electromagnetic energy applied via electrodes. For example, a radio frequency (RF) electrode may be used. The RF electrode may be the inner structure or the open body. Where a tank is also present then this may also be an electrode. In one example the inner structure and/or the tank are used as ground electrode and the open body to be treated is used as the RF electrode. An alternative arrangement involves the use of the tank and/or the inner structure as the RF electrode while the open body becomes the ground electrode. Yet another design may involve the use of either the tank or the inner structure as the RF electrode, and the other (tank or inner structure) as the ground electrode while the open body to be treated is not used as an electrode. If the tank is used as an RF electrode and the inner structure as the ground electrode, the hollow cathode effect may be formed, which can lead to high coating deposition rate. In order to allow for best distribution of gas used in relation to PECVD the inner structure may have a double wall construction with a solid inner wall to contain the treatment fluid and a perforated outer wall to enhance the distribution of gas. The solid inner wall and/or the perforated outer wall of the inner structure may act as an electrode. Where a tank is used then it may have a double wall construction with a solid outer wall to contain the treatment fluid and a perforated inner wall to enhance the distribution of gas. The solid outer wall and/or the perforated inner wall of the tank may act as an electrode. The various inner and outer walls may take the form of concentric cylinders for treating a generally cylindrical open body.

The various steps discussed above may be applied in sequence or at the same time. For example a combination of centrifugation and simultaneous UV radiation might be used, or a sequence of compression and heating. Any required combination could be used depending on the required treatment effect.

The method may comprise draining the treatment fluid from the inner and outer spaces, preferably to a reservoir so that excess treatment fluid may be stored and reused as needed. The treatment fluid itself may be expensive and/or may have a limited lifetime once exposed e.g. to the atmosphere or the tank. It may therefore be desirable to collect the excess treatment fluid in order to prevent it being discarded and to reuse it and hence improve cost efficiency of the treatment.

In situations where a uniform treatment is of primary concern then the inner structure may be arranged such that the treatment fluid inner volume spans less than 40% or less than 20% of the width of the interior of the open body, and the inner space is sized accordingly. The volume of treatment fluid may be a lesser concern in such examples, such as when a plasma or other low pressure fluid is used and the absolute quantities of materials is relatively low. In this case the over-riding consideration may be uniformity of the treatment process, which may require a specific distance between the open body and the inner structure. The tank, where present, may be arranged such that the treatment fluid outer volume spans less than 20% of the width of the interior of the tank, and the outer space is sized accordingly.

In other cases the volume of the treatment fluid may be of more significance, especially where costly liquids are used, and in those situations the inner structure may be arranged such that the treatment fluid inner volume is less than 50% of the volume of the interior to the open body, optionally less than 20% of the volume of the interior of the open body, optionally less than 10% and optionally less than 5%, and the inner space may be sized accordingly. The tank may be arranged such that the treatment fluid outer volume is less than 20% of the volume of the interior of the tank, optionally less than 10% and optionally less than 5%, and the outer space may be sized accordingly. In this way, a greatly reduced volume of treatment fluid is required to treat the surface of the open body, than would be needed without the present invention. The width of the space that confronts the surface of the open body, which can be an even width as discussed above, may be selected to provide the required volume.

For a PECVD system in which plasma is generated in situ, it may be desirable to have the treatment fluid inner volume occupy as much as 60% or more of the volume of the interior of the open body in order to have a more efficient plasma treatment. Similarly, the treatment fluid outer volume may also be as much as 60% of the volume of the interior of the tank.

The treatment fluid may be a first treatment fluid, and the method may comprise introducing a second fluid to the treatment volume and applying the second treatment fluid to the surface of the open body. The second fluid may displace the first fluid, or alternatively the first fluid may be removed before the second fluid is introduced. There may be a cleaning and/or flushing step between the two treatment steps. The treatment may be different for each treatment fluid. For example, the first treatment may clean the open body and the second treatment may coat it. The treatment may also be the same for each treatment fluid. The treatment fluid in each case could be any treatment fluid as mentioned herein, and application of the first treatment fluid and/or second treatment fluid may include the use of one or more steps such as sonication, UV treatment, heating, centrifugation, compression and so on. A third treatment and optionally further treatments may be included using further treatment fluids which may be the same or different to the first and/or second fluids. Any suitable combination of treatments may be applied to the open body by the disclosed method.

The method may include the use of any or all features of the system described below in order to carry out any or all of the steps described above.

According to a second aspect of the present invention there is provided a system for applying a treatment fluid to a surface of an open body, the system comprising; an inner structure shaped to complement the shape of the interior of the open body and to fill a major portion of the volume of the inner body; wherein the open body and the inner structure cooperate to define a treatment fluid inner volume comprising an inner space confronting an inner surface of the open body for introduction of a treatment fluid for contact of the treatment fluid with the inner surface.

The system may be arranged to operate in accordance with the method of the first aspect and/or optional features thereof as set out above. The inner surface may be a portion or the whole of the inner surface of the open body. The major portion of the volume of the inner body or the major portion of the width of the open body may be as discussed above.

The inner structure may be inflatable, and may be configured to be inflated within the open body. The inner structure may be shaped to complement the interior shape of the open body in its inflated state. Alternatively, the inner structure may be rigid. If rigid, the inner structure may be solid or may be hollow, or hollow, or partially hollow. If a hollow or partially hollow rigid structure, the inner structure may comprise a valve to allow gas from within the inner structure to escape in the event that pressure within the inner structure exceeds a predetermined limit, for example during heating of the treatment fluid and/or open body as described above in relation to the first aspect.

The system may comprise a tank shaped to complement and contain the open body; wherein the tank and the open body cooperate to define a treatment fluid outer volume comprising an outer space confronting the outer surface of the open body for introduction of a treatment fluid.

The system may therefore define a space between the tank and the inner structure which complements the shape of the open body, and which is then divided into the inner space and outer space by the open body when the open body is introduced therein, as described above in relation to the optional features of first aspect. The inner and outer spaces may be in fluid communication during use, either via holes and/or pores in the open body (e.g. if the open body comprises a mesh), or via a portion of the space between the tank and the inner body that is not divided by the open body, for example near the opening of the open body.

The system may comprise a lid for sealing the tank and the treatment fluid within the inner and outer spaces, wherein the lid optionally comprises an inlet for introducing the fluid into the treatment fluid inner volume and/or the treatment fluid outer volume. The tank may have an inlet located away from the lid for introducing fluid into the inner volume and/or outer volume. The inlet may also or alternatively be configured to be an outlet for removing fluid if required, for example to generate a vacuum or low pressure within the inner and outer spaces. A low pressure within the inner and outer spaces may aid in applying the treatment fluid to the open body, for example by improving the delivery of treatment fluid to openings or pores in the surface of the open body. The method of the first aspect may include the use of a lid as described above.

The system may comprise a hollow base, wherein the inner structure and tank are mounted on the hollow base, and wherein the hollow base comprises perforations for fluid exchange between the hollow base and treatment fluid inner and outer volumes. The hollow base may be suitable for draining excess fluid from the treatment fluid inner and outer volumes, for example after application of the treatment fluid to the surface of the open body. The interior volume of the hollow base may therefore be greater than the volume of the space between the tank and the inner structure. The hollow base may comprise an inlet/outlet to supply the excess treatment fluid to a treatment fluid reservoir, so that excess treatment fluid may be stored and reused as needed. The inlet/outlet may also be configured to permit the supply of fluid from the reservoir to the interior hollow base for application to the surface of the open body. The method of the first aspect may include the use of a hollow base as described above.

The system may be arranged to rotate the inner volume and/or outer volume, for example by rotation of one or more of the open body, the inner structure and/or the tank (where present). Thus, the system may be arranged to apply centrifugation to the treatment fluid in order to promote interaction of the treatment fluid with the surface of the open body.

The system may be arranged to compress the treatment fluid, for example by application of pressure to the fluid via an inlet to the volume, by expansion of the inner structure and/or by contraction of the tank (when present).

In some examples the system is arranged to apply a plasma as a treatment fluid, for example in context of plasma enhanced chemical vapour deposition (PECVD). The inner volume may be joined to a plasma generator so that it can receive plasma from the plasma generator. Alternatively the system may be arranged to generate a plasma within the treatment fluid volume via electromagnetic energy applied via electrodes. For example, an RF electrodes may be used. The RF electrode may be the inner structure or by the open body. Where a tank is also present then this may also be an electrode. In one example the inner structure and/or the outer structure are used as ground electrode and the open body to be treated is used as the RF electrode. An alternative arrangement involves the use of the tank and/or the inner structure as the RF electrode while the open body becomes the ground electrode. Yet another design may involve the use of either the tank or the inner structure as the RF electrode, and the other (tank or inner structure) as the ground electrode while the open body to be treated is not used as an electrode. If the tank is used as an RF electrode and the inner structure as the ground electrode, the hollow cathode effect may be formed, which can lead to high coating deposition. In order to allow for best distribution of gas used in relation to PECVD the inner structure may have a double wall construction with a solid inner wall to contain the treatment fluid and a perforated outer wall to enhance the distribution of gas. The solid inner wall and/or the perforated outer wall of the inner structure may act as an electrode. Where a tank is used then it may have a double wall construction with a solid outer wall to contain the treatment fluid and a perforated inner wall to enhance the distribution of gas. The solid outer wall and/or the perforated inner wall of the tank may act as an electrode. The various inner and outer walls may take the form of concentric cylinders for treating a generally cylindrical open body. The use of perforated wall maybe be needed for uniform fluid distribution in other systems other than PECVD The tank and/or inner structure may be double-walled and may contain at least one of a heating element, an ultrasonic transducer, a plasma generator or electrode, a heat insulating material, or an ultraviolet emitter. The inner wall of the tank and/or the outer wall of the inner structure may therefore be suitable for transmission of the emissions from any such components. That is, the walls may have a high heat conductivity to transmit heat to the treatment fluid and/or open body, may be formed of material which efficiently transmits ultrasonic vibrations, or may be substantially transparent to ultraviolet radiation, as required. Portions of the walls may be configured to transmit emissions from components as needed. A double wall construction with a perforated wall may be used in context of a plasma treatment as discussed above.

The inner structure and tank may define an annulus therebetween. That is, the inner structure and the tank may be substantially cylindrical, with the inner structure having a smaller radius than the tank. The open body may be an open cylinder, and be open at one end or both ends thereof, with a radius less than that of the tank and greater than that of the inner structure. The inner structure and tank may define any suitable volume therebetween to complement the shape of the open body. For example, the volume need not be circular and instead might be a polygonal shape or any other kind of shape.

The system may comprise a plurality of concentric cylinders nested, narrower cylinders being disposed within wider ones, so as to provide a plurality of annuli which may then accommodate open bodies with different radii. Each of the plurality of concentric cylinders may be mounted to a hollow base, and the hollow base may include perforations therein grouped into concentric rings to permit fluid communication between the hollow base and each of the plurality of annuli. The perforations in the hollow base may be opened and closed as required so as to permit fluid transfer to each of the plurality of annuli as required. A lid may be provided to seal all of the annuli simultaneously and prevent treatment fluid from transferring between any and each of the concentric annuli.

The system may be portable so as to be deployable in the field for routine maintenance or installation. Functionalization includes not only creating chemical groups that can enhance coating adhesion, but also includes applying materials (e.g. catalysts), either as discrete nanoparticles evenly spread across the surface of the open body or throughout the pores and crevices of a filter membrane, for example, or as a continuous film/coating. In addition to fluid, plasma can be used to functionalise an object. Note that the term treatment fluid used herein includes plasma.

The treatment fluid may comprise a nanocoating, and before application of the nanocoating, the open body may be dipped in a solution (e.g. an alkaline solution) in order to make it hydrophilic and hence aid in wetting of the surface.

Certain preferred embodiments of the invention will now be described by way of example only and with reference to the accompanying drawings in which.

Figure 1:
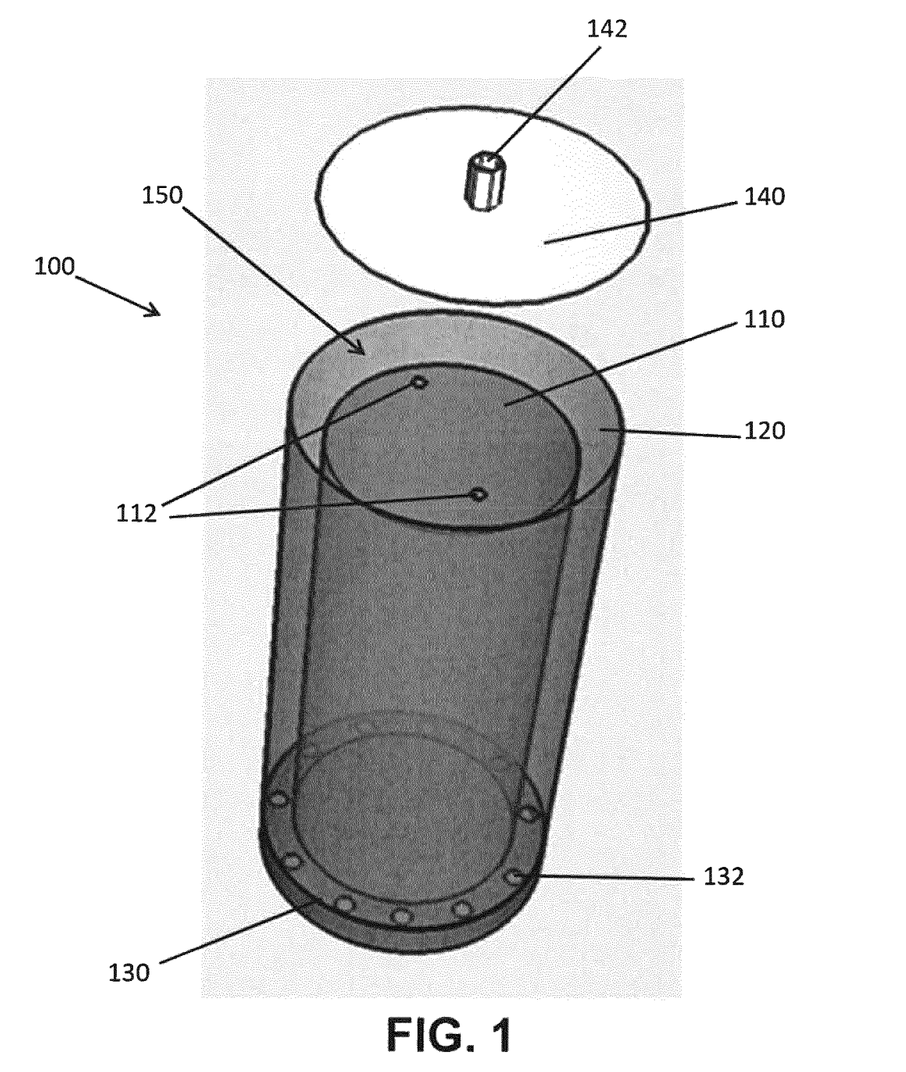
FIG. 1 shows a system for applying a treatment to an open body.

FIG. 1 shows an example of a system 100 for applying a treatment to a surface of an open body. The system is for treatment of surfaces of an open body (not shown) and includes an inner structure 110, a tank 120, a hollow base 130, and a lid 140.

The inner structure 110 and the tank 120 are both cylindrical, with the inner structure 110 having a smaller radius than the tank 120. The inner structure 110 is disposed concentrically within the tank 120 and consequently defines an annular space 150 which extends along the lengths of the inner structure 110 and tank 120. The inner structure 110 may be the same length or shorter than the tank 120, so that it does not extend beyond the opening of the tank 120.

The open body is a cylinder which is open at least one end, and has a radius greater than that of the inner structure 110 and less than that of the tank 120. The annular space 150 is therefore sized to received and accommodate the cylindrical open body. The cylindrical open body may be formed of a mesh, or any other desired material which has an overall cylindrical shape.

The cylindrical open body may therefore be inserted into the annular space 150 so that it surrounds the inner structure 110 such that the inner structure 110 fills a major portion of the open body, or a major portion of the width of the open body, and so that the open body is within the tank 120. Thus, during use, the open body is nested within the annular space 150 and between the tank 120 and inner structure 110. In FIG. 1, the inner structure 110 is shorter than the tank 120 so that the base of the cylindrical open body (which is closed at one end) is disposed within the tank 120.

The system also comprises the hollow base 130. The inner structure 110 and tank 120 are mounted on the hollow base 130 such that the hollow base 130 closes the bottom ends thereof. The hollow base 130 also comprises perforations 132 arranged in a ring to permit fluid communication between the interior of the hollow base 130 and the annular space 150. The perforations 132 may be opened or closed as needed, for example by an external controller.

The lid 140 is provided to seal the tank 120 and thereby retain fluid within the annular space 150. The lid 140 is provided with a lid inlet/outlet 142 for supply or removal of fluids—including gasses—to and from the annular space during use. The lid inlet 142 may also be configured to connect to a vacuum pump to reduce pressure within the annular space 150 to aid application of the treatment fluid to the open body. Although FIG. 1 shows only the single multifunctional lid inlet 142, a separate pump valve may be supplied on the lid to connect to a vacuum pump to reduce pressure within the annular space during application of the treatment to the open body, and to help draw treatment fluid into the annular space 150 from the hollow base 130.

In FIG. 1, the inner structure 110 comprises pressure valves 112, which are provided to permit high pressure gas within the inner structure 110 to be vented therefrom in the event that it exceeds a predetermined pressure. The inner structure 110 is therefore hollow. Such valves are of course not required if the inner structure is solid throughout. The pressure within the inner structure 110 may exceed a desired limit for example during a step of heating the treatment fluid and/or the open body within the annular space. The pressure valves 112 therefore prevent explosion of the inner structure 110 caused by excessive internal pressure. The pressure valves may be configured to open by mechanical or electrical means, enabling the purging of the pressure within the inner structure with a particular gas when necessary. If the inner structure 110 is hollow, it is of course closed to prevent treatment fluid from entering into it during use.

Therefore, once the cylindrical open body has been inserted within the annular space 150, the lid 140 is attached to the tank 120 to seal the space within the tank 120. The base of the cylindrical open body rests atop the inner structure 110, and may be held in place by fixture of the lid 140 to the tank 120, thereby retaining the cylindrical open body in place. Sealing of the lid 140 can be accomplished by application of a vacuum pump to the lid inlet/outlet 142, or by other mechanical means such as a threaded seal with o-ring seal.

The cylindrical open body thus divides the annular space 150 into an inner space (between the wall of the open body and the inner structure) and an outer space (between the wall of the open body and the tank 120). Two rings of perforations 132 may be used to separately serve the inner and outer spaces, when they are not supposed to be in fluid communication. The cylindrical open body may or may not extend to the hollow base 130.

Figure 2:
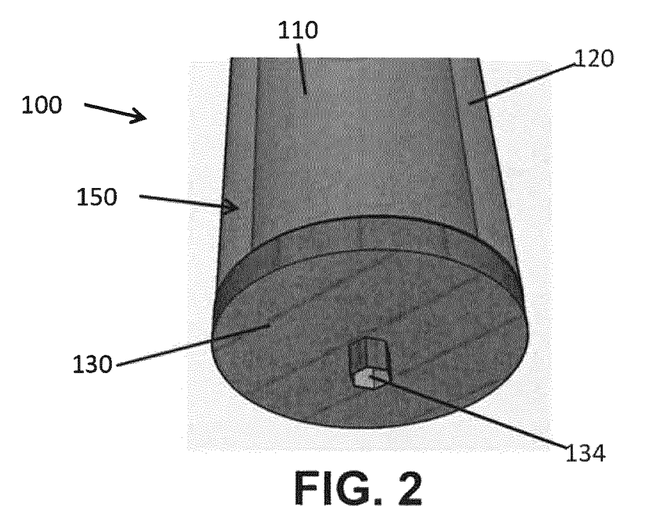
FIG. 2 shows a view of the system of FIG. 1.

FIG. 2 shows another perspective of the system 100 from beneath the hollow base 130. An inlet/outlet 134 of the hollow base 130 is visible in FIG. 2. This is provided to allow fluid to be transferred in and out of the interior of the hollow base 130 to and from a reservoir (not shown).

To introduce treatment fluid which is liquid into the annular space, the lid inlet/outlet 142 is connected to a vacuum pump while the hollow base 130 inlet/outlet 134 is connected to the reservoir of treatment fluid. The application of a vacuum from the lid inlet/outlet 142 can be used to simultaneously seal the device—with the lid—and to help in evacuating pockets of gas—e.g. air in a porous open body—in order to promote better wetting of the surface of the open body. However, introduction of the liquid may be delayed until such a time as an acceptable vacuum has been achieved. Both the lid inlet/outlet 142 and the hollow base inlet/outlet 134 can be fitted with valves and adapters to enable multiple connections thereto, as required. If a gas or plasma is to be introduced into the into the annular space 150, either of lid inlet/outlet 142 or hollow base inlet/outlet 134 can be used to supply the gas/plasma to the annular space 150 after the pressure in the sealed tank 120 has been reduced to a desired level.

External overpressure safety valves may be provided for the tank 120 (not shown in the figures), for example on the lid 140, on the external circumference of the tank 120, and/or on the external surface of the hollow base 130. Such external overpressure/safety valves may be needed during heating of the system to a temperature which may pose a risk of explosion, when such a heating step is not accompanied by a continuous inflow and outflow of gas to keep pressures regulated.

After the treatment fluid is introduced into the annular space 150, then various methods may be applied to aid the application of the fluid to the surface of the open body and to apply the treatment thereto. For example, the inner structure 110 may be configured to spin relative to the tank 120, and thereby exert pressure on the fluid in the annular space 150 and aid in introducing the treatment fluid to pores and crevices of the open body. The whole system may rotate to induce centrifugal forces in the fluid. Ultraviolet (UV) light may be applied to the treatment fluid which has been applied to the surface of the open body in order to cure the coating. Similarly, heat may be applied to the annular space 150 to aid in applying the treatment fluid or in curing a coating on the open body. Plasma may be applied to the annular space 150 in order to cause monomers introduced in or as the treatment fluid to polymerise on the surface of the open body and form a polymer. This may be done after excess treatment fluid (monomer) has been purged. Ultrasonic waves may also be applied to the annular space 150, again to aid in application of the treatment fluid to the surface of the open body. The fluid may be compressed during the treatment process. Such methods can be helpful in ensuring even application of the treatment fluid to the entire surface of the open body, particularly if the open body comprises small pores which might otherwise resist the introduction of fluid thereto.

The inner structure 110 and/or tank 120 may be double-walled, which then permits installation of components within the walls of tank 120 and/or inner structure 110. For example, insulation material, heating elements, ultraviolet (UV) light emitters, plasma generator/inlet, or ultrasound emitters may be installed therein as required. In this case, the walls of each of the inner structure 110 and the tank 120 may be designed to allow access to the space therebetween in order to service or replace components. The hollow base 130 may also be designed to provide access to the interior thereof for e.g. servicing the wiring controlling the perforations 132.

If UV light is to be used, the concentric cylinders may be made of quartz or other materials with low absorption and high transmission of low wavelength UV light. For a system with UV emitters installed, the outer periphery of the tank 120 may be covered with UV light-shielding material. The lid 140 and hollow base 130 may be made of materials opaque to UV light. Flexible (concentric) UV LEDs can be installed in between the walls of the double walled concentric cylinders and used to cure coatings, enable coating deposition or functionalization, or clean the open body.

Moderate or high heating of the treatment fluid or coated open body can be accomplished by heating elements attached to the outer periphery of the tank, the bottom end of the hollow base, on a support on which the hollow base 130 is standing, or in inside the hollow inner structure. The heating principle can be joule or induction heating.

Ultrasonic generators/transducers are preferably attached to the bottom of the hollow base 130, but they can also be attached to the outer periphery of the tank 120 or on top of the lid 140. The ultrasonic transducer will typically have a circular surface for emitting ultrasound, and when attached to the bottom of the hollow base, this circular shaped surface can have maximum, direct interaction with the liquid to be subjected to ultrasonication. It is preferable to maximize the surface of interaction of the ultrasonic transducers by keeping them in a straight line of action with the fluid to be subjected to ultrasonication. This helps minimize the loss of ultrasonic power.

The lid 140 and hollow base 130 may be made of transparent material if required. The hollow base 130 may preferably be made of steel or other appropriate metal in order to transmit ultrasonic waves to the treatment fluid. The hollow base 130 aids in introducing treatment fluid under vacuum (the lid inlet/outlet 142 is used to hold the system in vacuum). Introducing a fluid, particularly a liquid, into the system in the region of the lid inlet/outlet 142 may lead to excessive introduction of the fluid into the vacuum pump. Hence, advantages arise from introduction of the treatment fluid via the hollow base 130 at the opposite end of the system.

It may be desirable to compress the open body by causing the inner structure 110 to expand its diameter and/or the tank 120 to decrease its diameter in order to force the treatment fluid into space in the surface of the open body. This is similar to centrifugation but has the added advantage of not forming foams in solution.

After the treatment fluid has been applied to the surface of the open body, the hollow base 130 allows drainage/removal of the treatment fluid annular space. Drainage of the treatment fluid may be accomplished by gravity, or by pumping a fluid from the lid inlet/outlet 142.

The system has an inlet/outlet at both ends, and hence permits bursts of high pressure gas to be sent through the annular space 150, which may then be used to help drain excess liquid from a coated article or to simply dry the open body. For example, high pressure gas may be introduced from the lid inlet/outlet 142 and exit the system from the hollow base outlet 134. In this case, the evenly spaced perforations 132 in the hollow base allow for an even distribution of pressure through the annular space. Spinning or rotating the open body, with or without high pressure gas, can also be used to drain excess liquid.

However, a system without a hollow base 130—the hollow base 130 replaced by e.g. a flat plate—may be used in the case where the functions of the hollow base 130 are not necessary. However, such a mode of operation can still be accomplished with a device with a hollow base 130. The perforations 132 of the hollow base 130 are controllable (can be opened and closed) by valves for example, so that when use of the hollow base 130 is not needed, the perforations 132 can be closed.

The thickness of the bottom of the hollow base 130 (where the ultrasonic transducers may be attached) is preferably 5 mm or less, and more preferably 2 mm or less. A thinner wall will lead to lower loss of ultrasonic power. The height of the hollow base 130 is preferably 50 mm or less, and more preferably 15 mm or less. A small height ensures that little volume of fluid or plasma is needed to fill the hollow base 130, thus preserving the utility of the device for reducing the overall amount of fluid needed for treating hollow articles. A size of about 15 mm or less is recommended as the minimum space or height of liquid between an ultrasonic transducer and an article to be subjected to ultrasonication in a liquid. The diameter of the hollow base 130 is at least equal to that of the tank 120, and may be larger if required.

The diameters and lengths of the inner structure 110 and tank 120 are variable, and may be adapted depending on the open body to be treated. The width of the annular space is preferably 20 mm or less, and more preferably 12 mm or less. The inner structure 110 and tank 120 may be made of either transparent or non-transparent (e.g. metal) materials. The use of metals will enable application of high temperature to the device.

Figure 3:
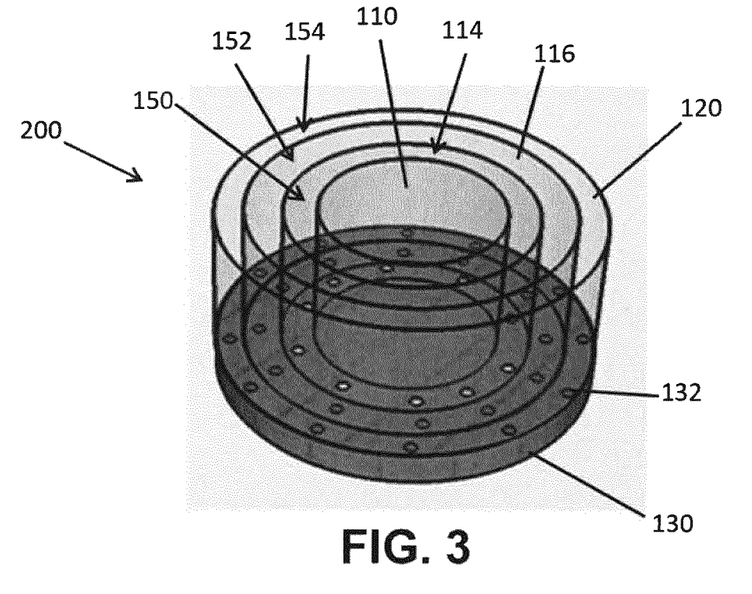
FIG. 3 shows another system for applying a treatment to an open body.

A system for applying a treatment to an open body may also comprise a plurality of systems as described above with incrementally varying widths, as shown in FIG. 3. Several concentric annuli with similar or varying widths can be incorporated into a single process unit where an open body can sequentially pass through a set of annuli. This can facilitate a higher rate of cleaning, functionalization or coating of several articles, or to carry out specific tasks in specific devices, e.g. having one annulus dedicated only to cleaning or to use of a particular fluid.

To handle open bodies of differing widths, a system may hence comprise a plurality of concentric cylinders 110, 114, 116 nested within one another inside a tank 120, the concentric cylinders 110, 114, 116 defining annuli 150, 152, 154 of differing widths, as shown in FIG. 3. The series of concentric cylinders 110, 114, 116 still share a common hollow base 130 and lid 140 (not shown). The perforations 132 may be controlled by e.g. a valve mechanism so that only a single one of the annuli 150, 152, 154 is supplied with treatment fluid. Alternatively, any combination of annuli 150, 152, 154 may be supplied simultaneously as needed.

The top of each annulus 150, 152, 154 may be provided with a locking mechanism for a corresponding lid with overpressure/safety valves, or a single lid may be supplied which simultaneously seals all annuli 150, 152, 154.

In a similar manner, a tank 120 may be provided with removable concentric cylinders 110, 114, 116 of varying width. The various concentric cylinders 110, 114, 116 may then be used to define a width of an annulus appropriate for the article to be treated.

The benefits of the above described method may also be achieved using an inflatable inner structure 110, shaped to complement the interior space of the open body when inflated. Therefore, when inflated inside the open body, the inflatable inner structure leaves a relatively narrow space between itself and the inner surface of the open body. This space may preferably be 10 mm or less, and/or may comprise 5% to 10% of the total volume of the interior space of the open body. With the inflated inner structure in place, the treatment fluid may then be introduced to fill the space between the inflated inner structure and the inner surface of the open body. As a result, the inner surface of the open body may be cleaned, functionalised or coated. These processes may also being enhanced or enabled by moderate heating, ultrasonication, UV exposure etc. as described above. The described method may reduce the amount of fluid needed for the cleaning, functionalization and/or coating processes by as much as 90-95%.

Figure 4:
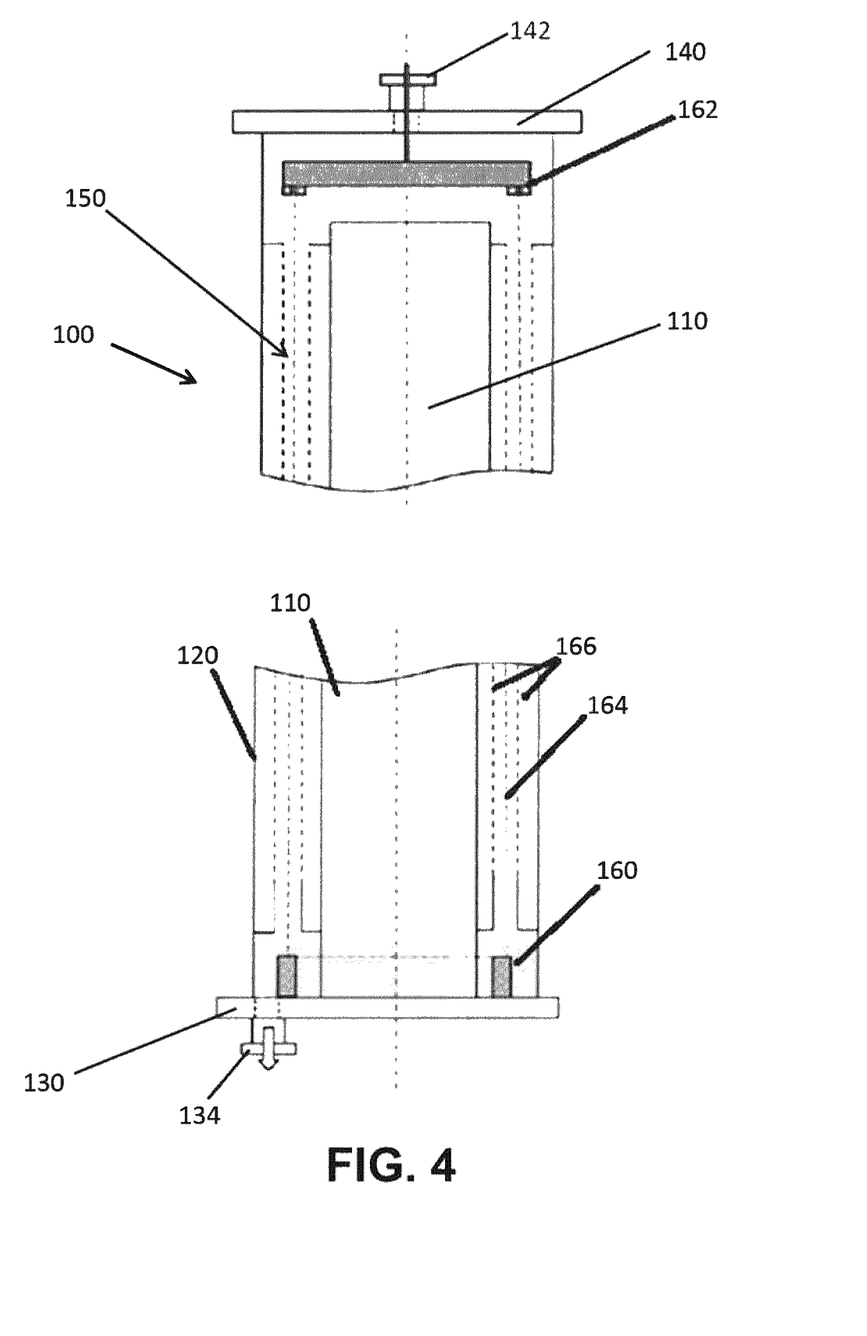
FIG. 4 shows a system for plasma enhanced chemical vapour deposition treatment of an open body.

FIG. 4 shows a system for plasma enhanced chemical vapour deposition (PECVD) treatment of an open body. In FIG. 4 the open body 164 to be treated is also shown in place within the annular space 150. In this example the open body 164 is a cylindrical screen filter. The system of FIG. 4 has a similar arrangement to the system of FIGS. 1 and 2 and thus has an inner structure 110, tank 120, annular space 150, lid 140, upper inlet/outlet 142, lower inlet/outlet 134 and base 130. The system of FIG. 4 includes a double walled construction for the inner structure 110 and the tank 120 with a perforated wall 166 extending toward the open body 164 from each of the inner structure 110 and the tank 120. The system further includes a spacer 160 to space the open body 164 away from the base 130 as well as a support 162 to hold the open body 164 in place. The support 162 also provide an RF connection to allow the open body 164 to act as an electrode, which may be its only function, that is it may not act as a support but a mere contact for RF input. In that case the spacer 160 acts as the only support. A DC bias voltage (not shown) may be applied to the open body 164 in order to improve coating quality. Gas may be supplied to the annular space 150 through swagelock gas inlets (not shown) on external surface of the PECVD system, for example on the tank. There may be multiple sets of swagelock gas inlets arrangement evenly spaced from each other in other to improve uniformity of gas distribution in the annular space 150.

The PECVD treatment may involve deposition (coating) on the open body 164, but it can also be used for cleaning and functionalisation, for example prior to a subsequent deposition process. The tank 120 and inner structure 110 are double walled as noted above, with the additional walls 166 (inner wall 166 for the tank 120 and outer wall 166 for the inner structure 110) being perforated to aid gas distribution. Gas injection from both sides of the open body 164 is used to allow for better coating uniformity. The lengths of the perforated walls 166 may be the same or different from those of the non-perforated ones 120, 110. There can optionally be more than two walls for each concentric cylinder in order to implement other operational needs, e.g. to allow for insulating materials or for equipment associated with other treatment processes as discussed above.

In a plasma treatment the perforated walls 166 and/or the non-perforated walls of the tank 120 and inner structure 110 can act as electrodes and thus are electrically connected to a suitable circuit. In this example they are grounded electrodes and the open body (screen filter) 164 acts as a radio frequency (RF) electrode, meaning it gets connected to a RF generator. It will be appreciated that the opposite arrangement of electrodes could also be used. RF is used to create the plasma within the annular space 150. This arrangement can ensure more uniform in treatment of all parts of the open body 164, especially in the sample of a screen filter 164 with pores that are micro or nano sized. The RF is normally 13.56 MHz, but lower and higher frequencies may be used. Higher frequencies have the advantage of faster deposition rate and better coating quality.

The spacer 160 may be a ceramic and may be at least 10 cm in height. This is used to prevent standing edge effects can affect coating uniformity and quality. It may be replaced by another suitable dielectric material which does not outgas, such as Teflon.

An example operation of the PECVD system of FIG. 4 is deposition of multilayer coating using the following steps:

1. Open chamber, insert the filter screen 164 and close the chamber.

2. Heat up the chamber to between 100 to 400° C., preferably at 150 to 200° C. For example, the chamber may be heated to about 200° C.

3. Start pumping to reduce the chamber to a desired based pressure, e.g. about 0.03 mbar.

4. Introduce argon and oxygen into until an operational pressure is attained, e.g. about 0.67 mbar.

5. Switch on the RF generator to apply RF in order to form a plasma (ionised gas molecules).

6. Clean and functionalise the walls of the screen filter using the plasma.

7. Introduce a combination of argon, silane ($SiH_4$) and ammonia ($NH_3$) in order to deposit silicon nitride $SiN_x$ to a thickness of 200 nm.

8. Switch to a combination of argon and other suitable gases to deposit $SiO_xC$ to a thickness of 30 nm.

9. Repeat the $SiN_x/SiO_xC$ deposition cycle for as many times as required.

10. Switch off plasma generator, stop heating, pump out gas, open chamber and unload the coated filter screen 164. With the PECVD system of FIG. 4 it becomes possible to uniformly coat a screen filter in a superior way to a conventional open chamber. Significant savings in energy may be derived in this PECVD design since less power is needed to bring the chamber down to a base pressure due to only applying vacuum to the concentric annulus 150 as opposed to evacuating a larger chamber. The same applies to the energy needed to heat up the concentric annulus. Savings in the amount of gases used are not as significant in relation to PECVD due to the very low pressures used. However, recycling of the waste gas can be significant, especially for long deposition runs. Thus the concentric annulus helps reduce the amount of energy, the amount of waste generated or capacity of the waste recycling system needed. The cycle time is also reduced by reducing the treatment volume.

By way of further example, a typical ballast water treatment system that utilizes electrochlorination requires a separator tank for removal of produced hydrogen. This tank is made of cathodically-protected 3161 stainless steel and is operated across a pH range of 2 to 11. As a result, both the steel tank and, especially the anode, are subject to severe corrosion and chemical attack, necessitating a frequent change of the sacrificial anode. An internal coating resistant to chemical attack in the above mentioned pH range is therefore important.

In a treatment of this separator tank using a system as in FIGS. 1 and 2 an inflatable inner structure 110 in the form of a deflated shaped balloon is introduced into the separator tank and inflated to assume a shape that is complementary to the tank's inner geometry, leaving only a small distance—the annular space 150—between the balloon (i.e. the inner structure) and the inner wall of the tank at any given point.

A 2M solution of sodium hydroxide is then introduced into the space, and heating and/or ultrasound applied for 20 minutes or less. This leaves the surface of the steel tank hydrophilic and covered with hydroxyl groups.

The sodium hydroxide is then removed and pure water used to rinse the tank, followed by drying. A $SiO_2$ based hybrid coating solution is then introduced and allowed to sit for five minutes, with or without heating and ultrasonication. Thereafter the solution is removed and the coating is allowed to dry.

The coating is then cured at 200° C. The coating is then annealed at 800° C. for 2 hours to convert it to a dense environmental barrier coating of $SiO_2$ (about 1 to 2 micrometer). This coating is hydrophilic.

As an optional step, another coating can be added to yield a hydrophobic layer on top of the $SiO_2$ layer.

In another example, a cylindrical filter screen made from 316 steel is subject to a coating process on both inner and outer surfaces of the filter screen, which has perforations between the inside and outside of the cylinder. The coating will also extend to all exposed surfaces around the perforations.

Step 1. The filter screen is concentrically placed in the annulus defined by two concentric cylinders as shown in FIG. 1, with distances of about 5 mm or less between the walls of the article and those of the concentric cylinders on either side.

Step 2. Vacuum is applied, and a cleaning solution is introduced. This can be soapy water. Ultrasound is used to help loosen dirt particles cling to the walls or the pores, crevices and outer peripheries of the filter screen. Heating (less than 100 degree Celsius, and preferably less than or equal to 80° C.), which enhances ultrasonic cleaning can also be used. The duration of this cleaning step can be 10 minutes or less. Thereafter the cleaning solution is flushed out under pressure. This step can be repeated until an acceptable level of cleaning is achieved. Then the solvent of the cleaning solution (e.g. water without soap) is introduced into the annulus and flushed out in order to rinse the article. Ultrasonication can also be employed in the latter. Step 2 can be skipped if the filter screen is a new one and hence cleaning is not needed.

Step 3: A functionalizing fluid is introduced into the treatment volumes around the filter screen. This is used to create hydrophilic groups (example hydroxyl groups) or other groups that have strong covalent attachment to the desired coating on the surface of the article (316 steel). These groups are important for strong coating adhesion. Making the surface hydrophilic is also important for the use of coating solutions involving a polar solvent, which is often the case. Prior to introducing this functionalizing fluid, the annulus can also be vacuumed as in step 2 above. When the functionalizing solution is in place, the ultrasound is turned on, with or without heating. This solution is preferably mildly concentrated sodium hydroxide, for example 2M solution. The functionalising medium can also be plasma, eliminating the need for ultrasonication and even heating. At the end of the functionalizing process with sodium hydroxide or any other solution, the article is rinsed with the solvent of the solution and dried using vacuum.

Step 4: A coating solution with a polar solvent is introduced into the annulus and thus fills the treatment volumes on the inner and outer surface of the filter screen. Pressure reduction at this stage may not be necessary because the surface of the article has been rendered hydrophilic. Depending on the coating solution, ultrasonication and/or heating can be used to enhance the coating process (deposition of the film). Afterwards, the coating solution is flushed out under pressure in order to remove excess liquid, allowing for conformal coating at a desirable coating thickness level.

Step 5: The coated article is brought out of the concentric chamber after 30 minutes and placed in an oven at 200° C. for curing (1 hour duration), leading to a strongly adhering hydrophobic coating. It may be desirable to afterwards anneal the article at higher temperatures, for example up to 800° C. or less (for example, for 2 hours) in order to form a dense environmental barrier inorganic coating, which is hydrophilic. The curing step can also be accomplished by heating the concentric arrangement, so that the article is brought out only after curing. This especially important when it is not desirable to expose the coated article to air or normal atmosphere before curing has been accomplished.

Note that steps 1 to 5 can be accomplished in a controlled atmosphere, for example inert atmosphere.

The methods and systems described herein hence provide improved methods and systems for applying a treatment to an open body. There is a significant reduction in the amount of treatment fluid needed for dip-coating of e.g. hollow cylinders with one or two of the ends open (pipes, drums, circular filter membranes, etc.). This is advantageous for expensive treatment fluid or plasma, including nanocoating. It is also useful for fluid which ages and becomes less useful with each dipping cycle/time. For example, in some cases only a small amount of the treatment fluid (e.g. less than 1%) is used in each cycle, so that much of the material will have to be discarded if the coating solution ages with time and use. The system and method is useful for routine R&D tests in which only a few objects may be coated in a given time period, which may otherwise leave behind a lot of unused fluid. The use of less fluid lessens the environmental impact/energy consumption when the fluid is discharged after being spent. The amount of energy needed to generate plasma is reduced, since a lesser amount of plasma is needed. Less space for storing fluid is also needed, since less fluid is ultimately needed.

The system has the capacity to coat the surface and pores of porous structures (e.g. filter membrane, anodize alumina, etc.) conformally without blocking the pores or causing an unwanted decrease in the sizes of the pores. This is accomplished with the use of e.g. vacuum, centrifugation, heating, spinning, compression or ultrasound in the annular space 150. It also has the capacity to significantly reduce the energy and materials needed for applying vacuum, centrifugation, heat, compression or ultrasound, compared to treating a structure (e.g. a pipe open at both end) in a space which does not utilize the annular arrangement. It also has the capacity to clean or functionalise (e.g. make hydrophilic, apply a catalyst) in a uniform and conformal manner the pores and crevices of a porous structure with treatment fluid or plasma. It also has the capacity to apply a vacuum or partial vacuum, spinning and high pressure gas in order to dry or remove excess fluid from the pores of an open body.

In further variations of the proposed method and system, the walls of the inserted inner structure 110 can be fitted with brushes (not shown in the Figures). The brushes could be used with an inflatable inner structure or a rigid inner structure 110. The handle of the brushes, which is firmly attached to the inner structure 110, can be activated to elongate or shorten the brush elements. This ensures that the bristles can be withdrawn so as not to obscure the inner wall of the structure to be treated, whereas when extended then the bristles can be placed in contact with the inner walls of the surface to be treated. Rotation or movement of the brushes or inner structure when the bristles are extended will apply brushing to enhance cleaning in conjunction with a cleaning fluid. The mechanism for elongation or shortening of the brush handles may not be needed if the insert is inflatable. In this case the inflation can be stopped short of the brushes touching the inner surface of the open body, followed by filling the inner space volume with the treatment fluid and complete inflation so that the brushes are in contact with the inner surface of the open body. This process will entail ejection of a small portion of the fluid already in the inner space volume if the treatment fluid is a liquid, or alternatively there may be compression of the treatment fluid.

In another optional feature, the walls of the inner structure 110 can be fitted with small pipes or nozzles (not shown in the Figures) that point to the direction of the inner walls of the article to be treated. The nozzles can be used to inject cleaning fluid straight against the surface of the inner walls of the open body, for example the injection of high pressure steam.

Treatment of an article with a liquid solution may also make use of an electrochemical action as the main or a complementary process for cleaning, functionalization or coating. This is particularly applicable if the article to be treated is electrically conducting. The outer wall of the inner structure 110 and/or the inner wall of the tank 120 can be made conducting by virtue of the material they are made of or by a thin film coating of a conductive material applied to them. They therefore can act as the counter electrode to the open body in order to subject the article to be treated to electrochemical actions. This therefore necessitates that the inner structure 110 and/or or tank 120 is not electrically in contact with the surface to be coated. The base of the concentric annulus (the upper end of the hollow base) could be made of a non-conducting material, or an insulation material can be placed between the article and the base of the annulus.

We claim:

1. A method of applying a treatment to a surface of an open body having a volume within an interior of the open body, the method comprising:
    providing an inner structure shaped to complement the shape of the interior of the open body and to fill a major portion of the volume or a major portion of a width of the interior of the open body;
    positioning the inner structure within the open body in order to form a treatment fluid inner volume comprising an inner space confronting an inner surface within the interior of the open body; and
    introducing a treatment fluid into the treatment fluid inner volume to thereby modify the inner surface of the open body by applying the treatment fluid thereto,
    wherein applying the treatment fluid comprises applying a plasma,
    and wherein the plasma is generated using the open body as an electrode.

2. The method as claimed in claim 1, wherein the inner structure is inflatable, and wherein the step of positioning the inner structure comprises inflating the inner structure.

3. The method as claimed in claim 1, wherein the inner structure is rigid, and therefore not inflatable.

4. The method as claimed in claim 1, comprising:
    providing a tank shaped to complement and contain the open body;
    positioning the open body within the tank in order to form a treatment fluid outer volume comprising an outer space confronting the outer surface of the open body; and
    introducing the treatment fluid into the treatment fluid outer volume to thereby modify the outer surface of the open body by applying the treatment.

5. The method as claimed in claim 4, wherein the tank is arranged such that the treatment fluid outer volume spans less than 20% of the width of the interior of the tank, and the outer space is sized accordingly.

6. The method as claimed claim 4, wherein the plasma is generated using either the inner structure or the tank as the other electrode.

7. The method as claimed in claim 1, wherein applying the treatment comprises coating, cleaning, or functionalizing the surface of the open body.

8. The method as claimed in claim 1, comprising applying ultrasonic waves and/or heat to the treatment fluid and/or open body; and/or comprising centrifugation and/or compression of the treatment fluid.

9. The method as claimed in claim 1, comprising applying ultraviolet (UV) radiation to the treatment fluid applied to the surface of the open body whilst the treatment fluid is present or after removal of the treatment fluid.

10. The method as claimed in claim 1, comprising aiding the introduction and/or removal of the treatment fluid by application of vacuum to the treatment fluid volume; and/or comprising aiding the introduction and/or removal of the treatment fluid by application of a high pressure fluid to the treatment fluid volume, and/or by spinning of the open body.

11. The method as claimed in claim 1, wherein the inner structure includes retractable brushes for brushing the inner surface of the open body and the method includes cleaning the inner surface using the brushes.

12. The method as claimed in claim 1, wherein the inner structure includes nozzles for applying a fluid to the inner surface of the open body.

13. The method as claimed in claim 1, comprising using an electrochemical action and/or a plasma to clean, functionalize or coat the open body.

14. The method as claimed in claim 1, wherein the inner structure is arranged such that the treatment fluid inner volume spans less than 20% of the width of the interior of the open body, and the inner space is sized accordingly; and/or wherein the treatment fluid is a first treatment fluid, the method comprising introducing a second fluid to the treatment volume and applying the second treatment fluid to the surface of the open body.

* * * * *